(12) United States Patent
Zhou et al.

(10) Patent No.: US 8,841,230 B2
(45) Date of Patent: Sep. 23, 2014

(54) PROCESSES FOR MAKING CATALYSTS WITH METAL HALIDE PRECURSORS

(75) Inventors: Zhenhua Zhou, Houston, TX (US); Heiko Weiner, Pasadena, TX (US)

(73) Assignee: Celanese International Corporation, Irving, TX (US)

( * ) Notice: Subject to any disclaimer, the term of this patent is extended or adjusted under 35 U.S.C. 154(b) by 8 days.

(21) Appl. No.: 13/595,381

(22) Filed: Aug. 27, 2012

(65) Prior Publication Data

US 2013/0178666 A1     Jul. 11, 2013

Related U.S. Application Data

(60) Provisional application No. 61/583,901, filed on Jan. 6, 2012.

(51) Int. Cl.
    *B01J 21/00*     (2006.01)

(52) U.S. Cl.
    USPC .......................................................... 502/260

(58) Field of Classification Search
    USPC ......... 502/224, 305, 254, 326, 250, 240, 262, 502/325, 352, 300, 260; 568/885
    See application file for complete search history.

(56) References Cited

U.S. PATENT DOCUMENTS

| | | | |
|---|---|---|---|
| 3,893,947 A * | 7/1975 | Young ............................ 502/220 |
| 4,199,438 A | 4/1980 | Antos et al. |
| 4,398,039 A | 8/1983 | Pesa et al. |
| 4,517,391 A | 5/1985 | Schuster et al. |
| 4,777,303 A | 10/1988 | Kitson et al. |
| 4,804,791 A | 2/1989 | Kitson et al. |
| 4,861,747 A | 8/1989 | Wachs et al. |
| 5,149,680 A | 9/1992 | Kitson et al. |
| 5,292,704 A | 3/1994 | Lester |
| 5,292,916 A | 3/1994 | Matsuzaki et al. |
| 5,719,097 A | 2/1998 | Chang et al. |
| 6,183,894 B1 | 2/2001 | Adzic et al. |
| 6,204,417 B1 | 3/2001 | Fisher et al. |
| 6,414,209 B1 | 7/2002 | Herskowitz et al. |
| 6,495,730 B1 | 12/2002 | Konishi et al. |
| 7,163,963 B2 | 1/2007 | Fraenkel |
| 7,608,744 B1 | 10/2009 | Johnston et al. |
| 8,080,694 B2 | 12/2011 | Weiner et al. |
| 2003/0105171 A1 | 6/2003 | Subramanian et al. |
| 2006/0241325 A1 | 10/2006 | Komplin et al. |
| 2008/0227627 A1 | 9/2008 | Strehlau et al. |
| 2009/0088317 A1 | 4/2009 | Frye, Jr. et al. |
| 2010/0029996 A1 | 2/2010 | Danjo et al. |
| 2010/0121114 A1 | 5/2010 | Weiner et al. |
| 2010/0197485 A1 * | 8/2010 | Johnston et al. ............... 502/241 |
| 2010/0197486 A1 | 8/2010 | Johnston et al. |
| 2011/0190117 A1 | 8/2011 | Weiner et al. |
| 2012/0209034 A1 | 8/2012 | Zhou et al. |
| 2012/0238785 A1 | 9/2012 | Zhou et al. |
| 2013/0178661 A1 | 7/2013 | Zhou et al. |
| 2013/0178662 A1 | 7/2013 | Zhou et al. |
| 2013/0178663 A1 | 7/2013 | Zhou et al. |
| 2013/0178664 A1 | 7/2013 | Zhou et al. |
| 2013/0178665 A1 | 7/2013 | Zhou et al. |
| 2013/0178667 A1 | 7/2013 | Zhou et al. |
| 2013/0178668 A1 | 7/2013 | Zhou et al. |

FOREIGN PATENT DOCUMENTS

| | | |
|---|---|---|
| EP | 0175558 | 3/1986 |
| EP | 0653242 | 5/1995 |
| EP | 1074299 | 2/2001 |
| FR | 2524339 | 10/1983 |
| JP | 11-147845 | 6/1999 |
| JP | 2001-046874 | 2/2001 |
| WO | WO 2007/107371 | 9/2007 |
| WO | WO 2011/053367 | 5/2011 |

OTHER PUBLICATIONS

T. Yokoyama, et al., "Carboxylic Acids and Derivatives", Fine Chemicals through Heterogenous Catalysis, pp. 370-379.
International Search Report and Written Opinion mailed Dec. 4, 2012 in corresponding International Application No. PCT/US2012/052499.
Office Action for U.S. Appl. No. 13/595,370 dated Sep. 26, 2013.
Office Action for U.S. Appl. No. 13/595,396 dated Dec. 13, 2013.

\* cited by examiner

*Primary Examiner* — Colleen Dunn
*Assistant Examiner* — Haytham Soliman

(57) ABSTRACT

The present invention relates to catalysts, to processes for making catalysts with halide containing precursors and to chemical processes employing such catalysts. The catalysts are preferably used for converting acetic acid to ethanol. The catalyst comprises a precious metal and one or more active metals on a support, optionally a modified support.

14 Claims, 3 Drawing Sheets

PROCESSES FOR MAKING CATALYSTS WITH METAL HALIDE PRECURSORS

CROSS REFERENCE TO RELATED APPLICATION

This application claims priority to U.S. Provisional App. No. 61/583,901, filed on Jan. 6, 2012, the entirety of which is incorporated herein by reference.

FIELD OF THE INVENTION

The present invention relates to catalysts, to processes for making catalysts with halide containing precursors, and to processes for producing ethanol from a feed stream comprising a carboxylic acid and/or esters thereof in the presence of the inventive catalysts.

BACKGROUND OF THE INVENTION

Ethanol for industrial use is conventionally produced from petrochemical feed stocks, such as oil, natural gas, or coal, from feed stock intermediates, such as syngas, or from starchy materials or cellulosic materials, such as corn or sugar cane. Conventional methods for producing ethanol from petrochemical feed stocks, as well as from cellulosic materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulosic material, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. The reduction of various carboxylic acids over metal oxides has been proposed by EP0175558 and U.S. Pat. No. 4,398,039. A summary some of the developmental efforts for hydrogenation catalysts for conversion of various carboxylic acids is provided in Yokoyama, et al., "Carboxylic acids and derivatives" in: *Fine Chemicals Through Heterogeneous Catalysis*, 2001, 370-379.

U.S. Pat. No. 6,495,730 describes a process for hydrogenating carboxylic acid using a catalyst comprising activated carbon to support active metal species comprising ruthenium and tin. U.S. Pat. No. 6,204,417 describes another process for preparing aliphatic alcohols by hydrogenating aliphatic carboxylic acids or anhydrides or esters thereof or lactones in the presence of a catalyst comprising Pt and Re. U.S. Pat. No. 5,149,680 describes a process for the catalytic hydrogenation of carboxylic acids and their anhydrides to alcohols and/or esters in the presence of a catalyst containing a Group VIII metal, such as palladium, a metal capable of alloying with the Group VIII metal, and at least one of the metals rhenium, tungsten or molybdenum. U.S. Pat. No. 4,777,303 describes a process for the productions of alcohols by the hydrogenation of carboxylic acids in the presence of a catalyst that comprises a first component which is either molybdenum or tungsten and a second component which is a noble metal of Group VIII on a high surface area graphitized carbon. U.S. Pat. No. 4,804,791 describes another process for the production of alcohols by the hydrogenation of carboxylic acids in the presence of a catalyst comprising a noble metal of Group VIII and rhenium. U.S. Pat. No. 4,517,391 describes preparing ethanol by hydrogenating acetic acid under superatmospheric pressure and at elevated temperatures by a process wherein a predominantly cobalt-containing catalyst.

Existing processes suffer from a variety of issues impeding commercial viability including: (i) catalysts without requisite selectivity to ethanol; (ii) catalysts which are possibly prohibitively expensive and/or nonselective for the formation of ethanol and that produce undesirable by-products; (iii) required operating temperatures and pressures which are excessive; (iv) insufficient catalyst life; and/or (v) required activity for both ethyl acetate and acetic acid.

SUMMARY OF THE INVENTION

The invention is directed to processes for forming catalysts. In a first embodiment the invention is to a process comprising the steps of: (a) preparing a first solution comprising a first metal halide and a second metal precursor comprising a second metal oxalate, acetate, halide, or nitrate; (b) preparing a second solution comprising a precious metal halide, oxalate, acetate or nitrate; (c) impregnating a support with the first solution and second solution to form an impregnated support; and (d) drying and calcining the impregnated support to form the catalyst. Preferably, the metal of the second metal precursor and precious metal halide, oxalate, acetate or nitrate is different than the metal of the first metal halide. The first and second solutions may be impregnated sequentially or simultaneously.

In a second embodiment the invention is to a process comprising the steps of: (a) preparing a first solution comprising a first metal halide and a second metal precursor comprising a second metal oxalate, acetate, halide, or nitrate; (b) preparing a second solution comprising a precious metal halide, oxalate, acetate or nitrate; (c) combining the second solution with the first solution to form a mixed metal precursor solution; (d) impregnating a support with the mixed metal precursor solution to form an impregnated support; and (e) drying and calcining the impregnated support to form the catalyst.

In a third embodiment the invention is to a process comprising the steps of: (a) preparing a first solution comprising a first metal halide; (b) combining a second metal precursor with the first solution to form a combined solution, wherein the second metal precursor comprises a second metal oxalate, acetate, halide, or nitrate; (c) preparing a second solution comprising a precious metal halide, oxalate, acetate or nitrate; (d) combining the second solution with the combined solution to form a mixed metal precursor solution; (e) impregnating a support with the mixed metal precursor solution to form an impregnated support; and (f) drying and calcining the impregnated support to form the catalyst.

In a fourth embodiment the invention is to a process comprising preparing a support modifier precursor solution comprising a metal selected from the group consisting of tungsten, molybdenum, niobium, vanadium, and tantalum, and one or more active metals; impregnating a support with the support modifier precursor solution; and dried and calcined as necessary to form the modified support. The process further comprises preparing at least two different solutions of metal precursors, provided that one of the different solutions comprises a metal halide precursor and at least one of the metals in the different solutions is the same as one of the active metals in the support modifier precursor solution, and impregnating the modified support with the different solutions to form an impregnated support. The impregnated support may be subsequently dried and calcined as necessary.

The support preferably is a modified support comprising a support modifier metal selected from the group consisting of tungsten, molybdenum, niobium, vanadium, and tantalum. The support preferably is a modified support comprising the first metal, the second metal and a support modifier metal selected from the group consisting of tungsten, molybdenum, niobium, vanadium and tantalum. The support preferably comprises support material selected from the group consisting of silica, alumina, titania, silica/alumina, pyrogenic silica, high purity silica, zirconia, carbon, zeolites and mixtures thereof. In other embodiments, the support may be a modified support comprising calcium metasilicate, as described in US Pub. Nos. 2010/0121114 and 2010/0197985, the entire contents and disclosure of which are hereby incorporated by reference. In exemplary embodiments, the support comprises silica and tungsten oxide, or silica and cobalt tungstate. Preferably, the support modifier does not comprise tin tungstate, even though the support modifier may comprise tin.

The precious metal preferably is selected from the group consisting of rhodium, rhenium, ruthenium, platinum, palladium, osmium, iridium and gold. The first metal optionally is selected from the group consisting of copper, iron, cobalt, vanadium, nickel, titanium, zinc, chromium, molybdenum, tungsten, tin, lanthanum, cerium, and manganese, more preferably selected from the group consisting of copper, tin, and cobalt. The second metal optionally is selected from the group consisting of copper, iron, cobalt, vanadium, nickel, titanium, zinc, chromium, molybdenum, tungsten, tin, lanthanum, cerium, and manganese. In one aspect, the precious metal is selected from the group consisting of rhodium, rhenium, ruthenium, platinum, palladium, osmium, iridium and gold, and the first metal and the second metal are selected from the group consisting of copper, iron, cobalt, vanadium, nickel, titanium, zinc, chromium, molybdenum, tungsten, tin, lanthanum, cerium, and manganese. In some embodiments, the precious metal is present in an amount from 0.1 to 5 wt. %, the first metal is present in an amount from 0.5 to 20 wt. % and the second metal is present in an amount from 0.5 to 20 wt. %, based on the total weight of the catalyst. In one embodiment, the support modifier, such as $WO_3$ or $V_2O_5$, may be in an amount from 1 to 40 wt. %, e.g., from 0.1 to 30 wt. % or from 10 to 25 wt. %.

In another embodiment, the invention is to a catalyst formed by the above-described process. The formed catalyst may have a halide concentration that is greater than 10 wppm, e.g., greater than 100 wppm or greater than 200 wppm.

In another embodiment, the invention is to a process for producing ethanol, comprising contacting a feed stream comprising acetic acid, hydrogen and optionally ethyl acetate in a reactor at an elevated temperature in the presence of the above described catalyst under conditions effective to form ethanol. The feed stream optionally comprises ethyl acetate in an amount greater than 5 wt. %. The process may provide an acetic acid conversion greater than 20%, e.g., greater than 50%, greater than 80% or greater than 90%, and an ethyl acetate conversion greater than 0%, e.g., greater than 5%, greater than 10% or greater than 15%. Acetic acid selectivity to ethanol may be greater than 80% or greater than 90%. In one aspect, the process forms a crude product comprising the ethanol and ethyl acetate, and the crude product has an ethyl acetate steady state concentration from 0.1 to 40 wt %, e.g., from 0.1 to 20 wt %, or from 0.1 to 10 wt %.

BRIEF DESCRIPTION OF THE DRAWINGS

The present invention will be better understood in view of the appended non-limiting figures, in which.

DETAILED DESCRIPTION OF THE INVENTION

The present invention is directed to processes for making catalyst compositions that preferably are suitable as hydrogenation catalysts, to processes for forming such catalysts, and to chemical processes employing such catalysts. The catalysts preferably comprise one or more active metals on a support, preferably a modified support, and may be suitable in catalyzing the hydrogenation of a carboxylic acid, e.g., acetic acid, and/or esters thereof, e.g., ethyl acetate, to the corresponding alcohol, e.g., ethanol.

In one embodiment, the inventive catalyst comprises a precious metal and one or more active metals on a support. Preferably the support is a modified support comprising a support material and a support modifier comprising a metal selected from tungsten, molybdenum, vanadium, niobium and tantalum. In one aspect, the modified support comprises one or more of the active metals that are also disposed on the support, i.e., one or more of the active metals are part of the modified support and also disposed on top of the modified support.

It has now been discovered that such catalysts are particularly effective as multifunctional hydrogenation catalysts capable of converting both carboxylic acids, such as acetic acid, and esters thereof, e.g., ethyl acetate, to their corresponding alcohol(s), e.g., ethanol, under hydrogenation conditions. Thus, in another embodiment, the inventive catalyst comprises a precious metal and an active metal on a modified support, wherein the catalyst is effective for providing an acetic acid conversion greater than 20%, greater than 75% or greater than 90%, and an ethyl acetate conversion greater than 0%, greater than 10% or greater than 20%.

Processes for Making the Catalyst

Figure 1:
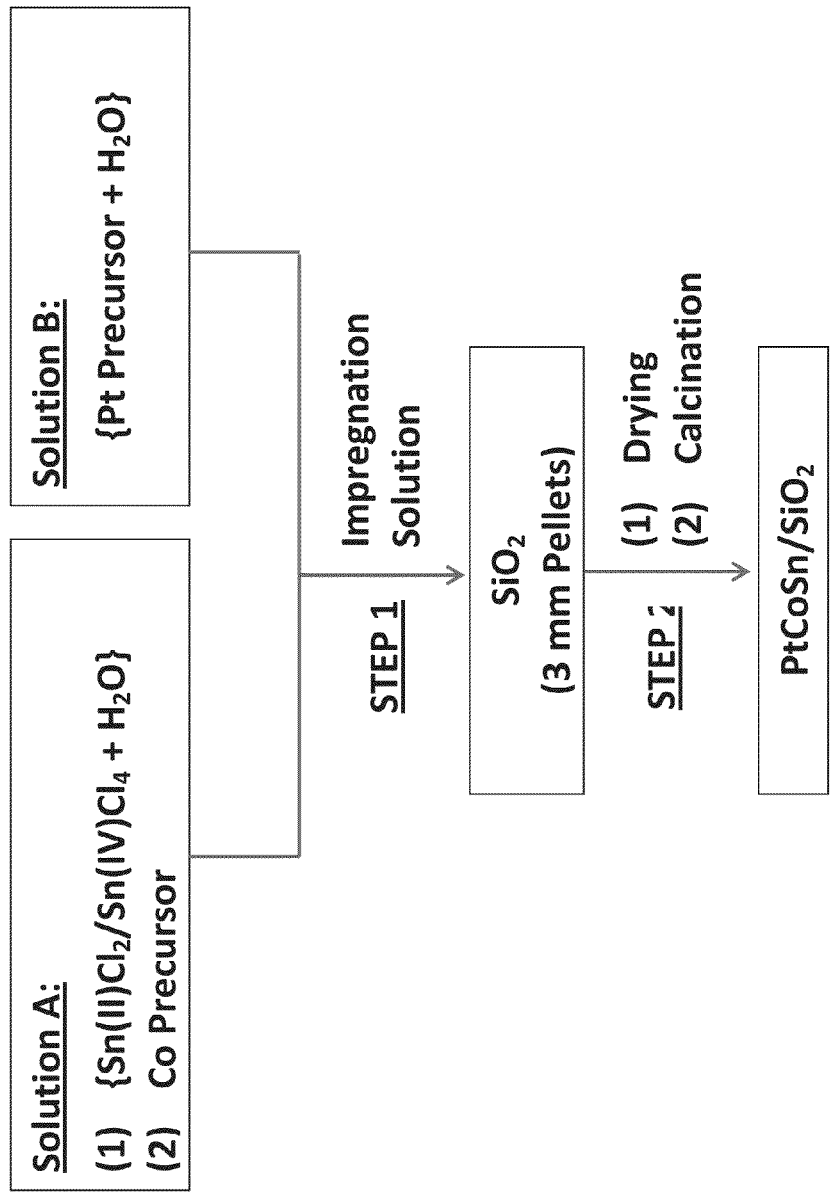
FIGS. 1-3 are exemplary flow diagrams for forming a catalyst according to embodiments of the present invention.
Figure 2:
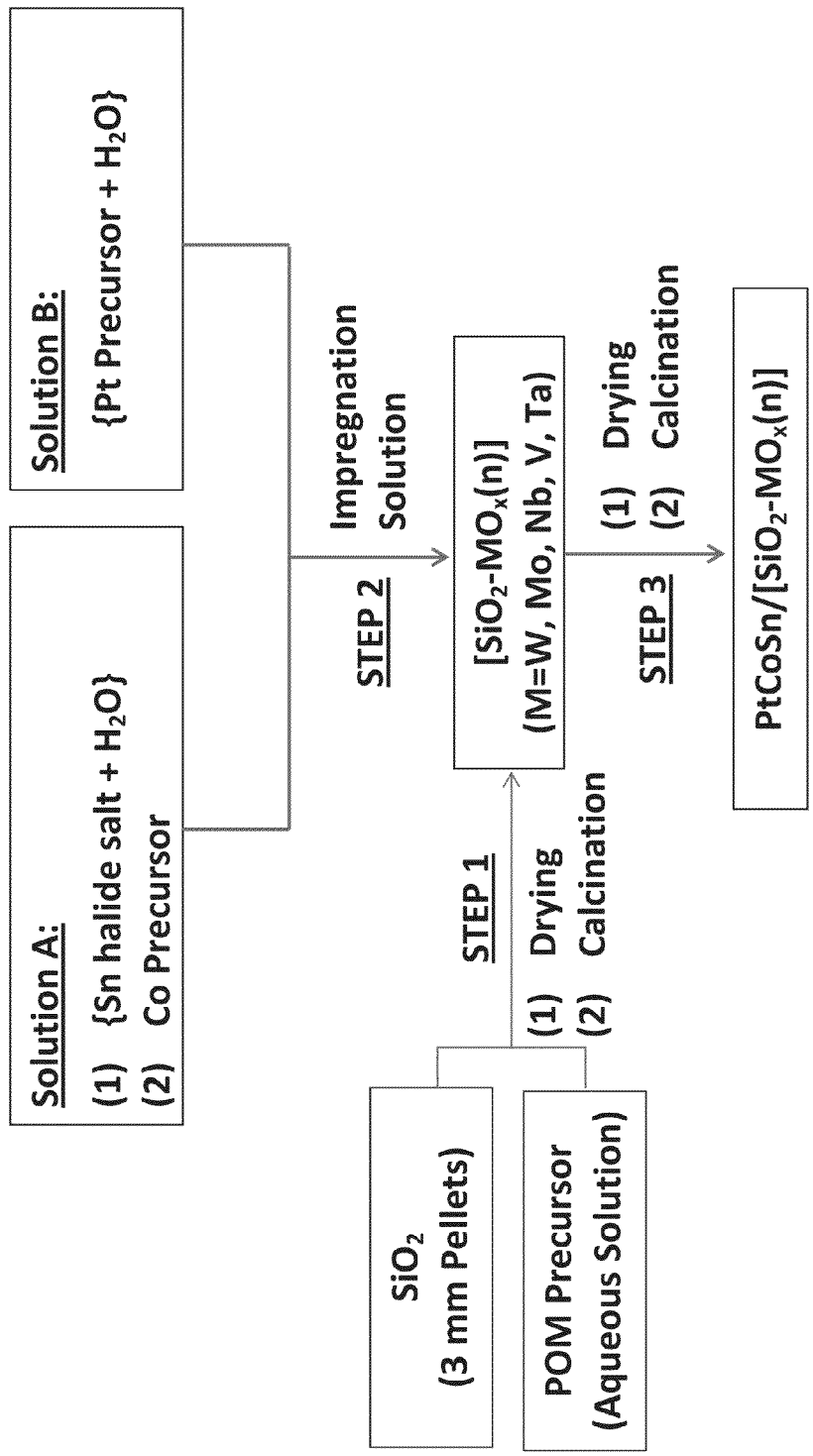
Figure 3:
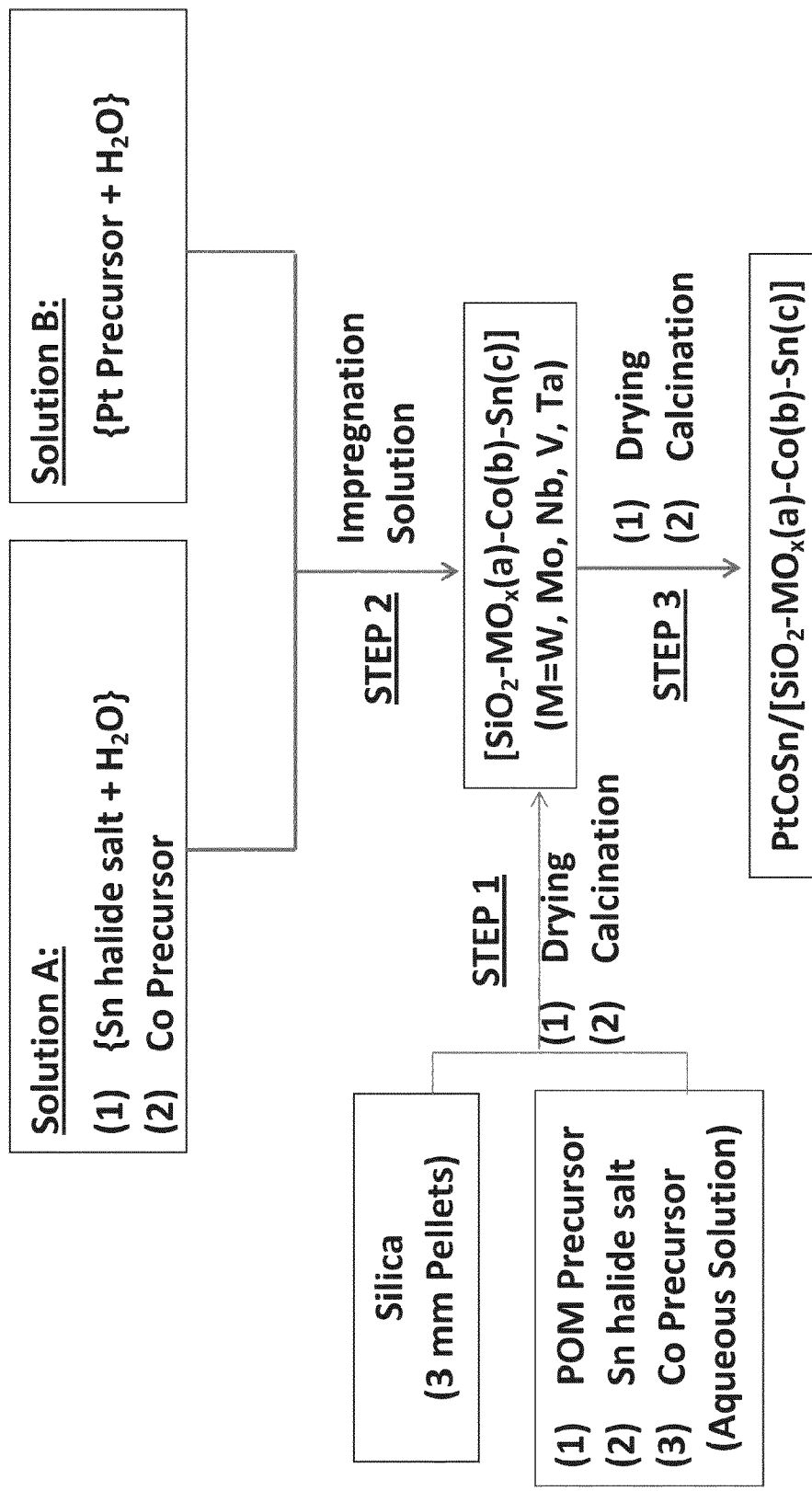

The present invention relates to processes for making the catalyst through an impregnation step with two different solutions of precursors, one which comprises a metal halide precursor. Preferably the metal halide is a tin metal halide. Without being bound by theory, the process for making the catalyst may improve one or more of acetic acid conversion, ester conversion, ethanol selectivity and overall productivity. FIGS. 1-3 provide exemplary summaries of the catalyst preparation protocols according to the present invention. In FIG. 1, two different solutions are impregnated on a silica support. In FIG. 2, two different solutions are impregnated on a silica support modified with tungsten. The modified support may be prepared in a first step followed by a sequential or simultaneous impregnation of the different solutions. In FIG. 3, two different solutions are impregnated on a silica support modified with tungsten, cobalt and tin. It should be understood that other metals and supports described herein may be suited for the exemplary metals and supports in FIGS. 1-3. In addition, although tin is shown as the metal halide, the other metals, e.g., cobalt or platinum, may be the metal halide.

In this embodiment, the support modifier solution may comprise a support modifier metal precursor and one or more active metal precursors, more preferably at least two active metal precursors. The precursors preferably are comprised of salts of the respective metals in solution, which, when heated, are converted to elemental metallic form or to a metal oxide. Since, in this embodiment, two or more active metal precursors are impregnated onto the support material simultaneously and/or sequentially with the support modifier precursor, one or more of the resulting active metals may interact with the support modifier metal at a molecular metal upon formation to form one or more polymetallic crystalline species, such as cobalt tungstate. In other embodiments, one or more of the active metals will not interact with the support modifier metal precursor and are separately deposited on the support material, e.g., as discrete metal nanoparticles or as an amorphous metal mixture. Thus, the support material may be modified with one or more active metal precursors at the same time that it is modified with a support modifier metal, and the resulting active metals may or may not interact with the support modifier metal to form one or more polymetallic crystalline species.

In some embodiments, the support modifier may be added as particles to the support material. For example, one or more support modifier precursors, if desired, may be added to the support material by mixing the support modifier particles with the support material, preferably in water. When mixed it is preferred for some support modifiers to use a powdered material of the support modifiers. If a powdered material is employed, the support modifier may be pelletized, crushed and sieved prior to being added to the support.

As indicated, in most embodiments, the support modifier preferably is added through a wet impregnation step. Preferably, a support modifier precursor to the support modifier may be used. Some exemplary support modifier precursors include alkali metal oxides, alkaline earth metal oxides, Group IIB metal oxides, Group IIIB metal oxides, Group IVB metal oxides, Group VB metal oxides, Group VIB metal oxides, Group VIIB metal oxides, and/or Group VIII metal oxides, as well as preferably aqueous salts thereof.

Although the overwhelming majority of metal oxides and polyoxoion salts are insoluble, or have a poorly defined or limited solution chemistry, the class of isopoly- and heteropolyoxoanions of the early transition elements forms an important exception. These complexes may be represented by the general formulae:

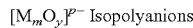
[M$_m$O$_y$]$^{p-}$ Isopolyanions

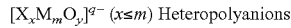
[X$_x$M$_m$O$_y$]$^{q-}$ ($x \leq m$) Heteropolyanions where M is selected from tungsten, molybdenum, vanadium, niobium, tantalum and mixtures thereof, in their highest (d$^0$, d$^1$) oxidations states. Such polyoxometalate anions form a structurally distinct class of complexes based predominately, although not exclusively, upon quasi-octahedrally-coordinated metal atoms. The elements that can function as the addenda atoms, M, in heteropoly- or isopolyanions may be limited to those with both a favorable combination of ionic radius and charge and the ability to form d$_\pi$-p$_\pi$ M-O bonds. There is little restriction, however, on the heteroatom, X, which may be selected from virtually any element other than the rare gases. See, e.g., M. T. Pope, *Heteropoly and Isopoly Oxometalates*, Springer Verlag, Berlin, 1983, 180; Chapt. 38, *Comprehensive Coordination Chemistry*, Vol. 3, 1028-58, Pergamon Press, Oxford, 1987, the entireties of which are incorporated herein by reference.

Polyoxometalates (POMs) and their corresponding heteropoly acids (HPAs) have several advantages making them economically and environmentally attractive. First, HPAs have a very strong approaching the superacid region, Bronsted acidity. In addition, they are efficient oxidants exhibiting fast reversible multielectron redox transformations under rather mild conditions. Solid HPAs also possess a discrete ionic structure, comprising fairly mobile basic structural units, e.g., heteropolyanions and countercations (H$^+$, H$_3$O$^+$, H$_5$O$_2^+$, etc.), unlike zeolites and metal oxides.

In view of the foregoing, in some embodiments, the support modifier precursor comprises a POM, which preferably comprises a metal selected from the group consisting of tungsten, molybdenum, niobium, vanadium and tantalum. In some embodiments, the POM comprises a hetero-POM. A non-limiting list of suitable POMs includes phosphotungstic acid (H—PW$_{12}$) (H$_3$PW$_{12}$O$_{40}$.nH$_2$O), ammonium metatungstate (AMT) ((NH$_4$)$_6$H$_2$W$_{12}$O$_{40}$.H$_2$O), ammonium heptamolybdate tetrahydrate, (AHM) ((NH$_4$)$_6$Mo$_7$O$_{24}$.4H$_2$O), silicotungstic acid hydrate (H—SiW$_{12}$) (H$_4$SiW$_{12}$O$_{40}$.H$_2$O), silicomolybdic acid (H—SiMo$_{12}$) (H$_4$SiMo$_{12}$O$_{40}$.nH$_2$O), and phosphomolybdic acid (H-PMo$_{12}$) (H$_3$PMo$_{12}$O$_{40}$.H$_2$O).

The use of POM-derived support modifiers in the catalyst compositions of the invention has now surprising and unexpectedly been shown to provide bi- or multi-functional catalyst functionality, desirably resulting in conversions for both acetic acid and byproduct esters such as ethyl acetate, thereby rendering them suitable for catalyzing mixed feeds comprising, for example, acetic acid and ethyl acetate.

Impregnation of the precious metal and one or more active metals onto the support, e.g., modified support, may occur simultaneously (co-impregnation) or sequentially. In simultaneous impregnation, the two or more metal precursors are mixed together and added to the support, preferably modified support, together followed by drying and calcination to form the final catalyst composition. With simultaneous impregnation, it may be desired to employ a dispersion agent, surfactant, or solubilizing agent, e.g., ammonium oxalate, to facilitate the dispersing or solubilizing of the first, second and/or optional third metal precursors in the event the two precursors are incompatible with the desired solvent, e.g., water.

In sequential impregnation, the first metal precursor may be first added to the support followed by drying and calcining, and the resulting material may then be impregnated with the second metal precursor followed by an additional drying step followed by a calcining step to form the final catalyst composition. Additional metal precursors (e.g., a third metal precursor) may be added either with the first and/or second metal precursor or in a separate third impregnation step, followed by drying and calcination. Of course, combinations of sequential and simultaneous impregnation may be employed if desired.

In embodiments where the precious metal and/or one or more active metals, e.g., one or more of the first, second or third metals, are applied to the catalyst sequentially, i.e., in multiple impregnation steps, the catalyst may be said to comprise a plurality of "theoretical layers." For example, where a first metal is impregnated onto a support followed by impregnation of a second metal, the resulting catalyst may be said to have a first theoretical layer comprising the first metal and a second theoretical layer comprising the second metal. As discussed above, in some aspects, more than one active metal precursor may be co-impregnated onto the support in a single step such that a theoretical layer may comprise more than one metal or metal oxide. In another aspect, the same metal precursor may be impregnated in multiple sequential impregnation steps leading to the formation of multiple theoretical layers containing the same metal or metal oxide. In this context, notwithstanding the use of the term "layers," it will be appreciated by those skilled in the art that multiple layers may or may not be formed on the catalyst support depending, for example, on the conditions employed in catalyst formation, on the amount of metal used in each step and on the specific metals employed.

The use of a solvent, such as water, glacial acetic acid, a strong acid such as hydrochloric acid, nitric acid, or sulfuric acid, or an organic solvent, is preferred in the support modification step, e.g., for impregnating a support modifier precursor onto the support material. When the precursor solution comprises a metal halide, the use of water, glacial acetic acid, or an organic solvent is preferred. The support modifier solution comprises the solvent, preferably water, a support modifier precursor, and preferably one or more active metal precursors. The solution is stirred and combined with the support material using, for example, incipient wetness techniques in which the support modifier precursor is added to a support material having the same pore volume as the volume of the solution. Impregnation occurs by adding, optionally drop wise, a solution containing the precursors of either or both the support modifiers and/or active metals, to the dry support material. Capillary action then draws the support modifier into the pores of the support material. The thereby impregnated support can then be formed by drying, optionally under vacuum, to drive off solvents and any volatile components within the support mixture and depositing the support modifier on and/or within the support material. Drying may occur, for example, at a temperature from 50° C. to 300° C., e.g., from 100° C. to 200° C. or about 120° C., optionally for a period from 1 to 24 hours, e.g., from 3 to 15 hours or from 6 to 12 hours. The dried support may be calcined, optionally with ramped heating, for example, at a temperature from 300° C. to 900° C., e.g., from 400° C. to 750° C., from 500° C. to 600° C. or at about 550° C., for a period of time from 1 to 12 hours, e.g., from 2 to 10 hours, from 4 to 8 hours or about 6 hours, to form the modified support. Upon heating and/or the application of vacuum, the metal(s) of the precursor(s) preferably decompose into their oxide or elemental form. In some cases, the completion of removal of the solvent may not take place until the catalyst is placed into use and/or calcined, e.g., subjected to the high temperatures encountered during operation. During the calcination step, or at least during the initial phase of use of the catalyst, such compounds are converted into a catalytically active form of the metal or a catalytically active oxide thereof.

Once formed, the modified supports may be shaped into particles having the desired size distribution, e.g., to form particles having an average particle size in the range from 0.2 to 0.4 cm. The supports may be extruded, pelletized, tabletized, pressed, crushed or sieved to the desired size distribution. Any of the known methods to shape the support materials into desired size distribution can be employed. Alternatively, support pellets may be used as the starting material used to make the modified support and, ultimately, the final catalyst.

In one embodiment, the precious metal and one or more active metals are impregnated onto the support, preferably onto any of the above-described modified supports. A precursor of the precious metal preferably is used in the metal impregnation step, such as a water soluble compound or water dispersible compound/complex that includes the precious metal of interest. Similarly, precursors to one or more active metals may also be impregnated into the support, preferably modified support. Depending on the metal precursors employed, the use of a solvent, such as water, glacial acetic acid, nitric acid or an organic solvent, may be preferred to help solubilize one or more of the metal precursors.

In one embodiment, separate solutions of the metal precursors are formed, which are subsequently blended prior to being impregnated on the support. For example, a first solution may be formed comprising a first metal precursor, and a second solution may be formed comprising the second metal precursor and optionally the third metal precursor. At least one of the first, second and optional third metal precursors preferably is a precious metal precursor, and the other(s) are preferably active metal precursors (which may or may not comprise precious metal precursors). Either or both solutions preferably comprise a solvent, such as water, glacial acetic acid, hydrochloric acid, nitric acid or an organic solvent.

In one exemplary embodiment, a first solution comprising a first metal halide is prepared. The first metal halide optionally comprises a tin halide, e.g., a tin chloride such as tin (II) chloride and/or tin (IV) chloride. Optionally, a second metal precursor, as a solid or as a separate solution, is combined with the first solution to form a combined solution. The second metal precursor, if used, preferably comprises a second metal oxalate, acetate, halide or nitrate, e.g., cobalt nitrate. The first metal precursor optionally comprises an active metal, optionally copper, iron, cobalt, nickel, chromium, molybdenum, tungsten, or tin, and the second metal precursor, if present, optionally comprises another active metal (also optionally copper, iron, cobalt, nickel, chromium, molybdenum, tungsten, or tin). A second solution is also prepared comprising a precious metal precursor comprising an oxalate, acetate, halide or nitrate. In this embodiment a precious metal halide, such as a halide of rhodium, rhenium, ruthenium, platinum or palladium, may be used. The second solution is combined with the first solution or the combined solution, depending on whether the second metal precursor is desired, to form a mixed metal precursor solution. The resulting mixed metal precursor solution may then be added to the support, optionally a modified support, followed by drying and calcining to form the final catalyst composition as described above. The resulting catalyst may or may not be washed after the final calcination step. Without being bound by theory, the halide precursors used in embodiments of the present invention may be easy to solubilize, and thus a solubility modifier, such as an acid or base, may not be required. Thus, the solutions comprising the metal halide precursor may be substantially free from acids such as acetic acid, hydrochloric acid or nitric acid.

In one embodiment, the impregnated support, optionally impregnated modified support, is dried at a temperature from 100° C. to 140° C., from 110° C. to 130° C., or about 120° C., optionally from 1 to 12 hours, e.g., from 2 to 10 hours, from 4 to 8 hours or about 6 hours. If calcination is desired, it is preferred that the calcination temperature employed in this step is less than the calcination temperature employed in the formation of the modified support, discussed above. The second calcination step, for example, may be conducted at a temperature that is at least 50° C., at least 100° C., at least 150° C. or at least 200° C. less than the first calcination step, i.e., the calcination step used to form the modified support. For example, the impregnated catalyst may be calcined at a temperature from 200° C. to 500° C., from 300° C. to 400° C., or about 350° C., optionally for a period from 1 to 12 hours, e.g., from 2 to 10 hours, from 4 to 8 hours or about 6 hours.

In one embodiment, ammonium oxalate is used to facilitate solubilizing of at least one of the metal precursors, e.g., a tin precursor, as described in U.S. Pat. No. 8,211,821, the entirety of which is incorporated herein by reference. In this aspect, the first metal precursor optionally comprises an oxalate of a precious metal, e.g., rhodium, palladium, or platinum, and a second metal precursor optionally comprises an oxalate tin. Another active metal precursor, if desired, comprises a nitrate, halide, acetate or oxalate of chromium, copper, or cobalt. In this aspect, a solution of the second metal precursor may be made in the presence of ammonium oxalate as solubilizing agent, and the first metal precursor may be added thereto, optionally as a solid or a separate solution. If used, the third metal precursor may be combined with the solution comprising the first precursor and tin oxalate precursor, or may be combined with the second metal precursor, optionally as a solid or a separate solution, prior to addition of the first metal precursor. In other embodiments, an acid such as acetic acid, hydrochloric acid or nitric acid may be substituted for the ammonium oxalate to facilitate solubilizing of the tin oxalate. The resulting mixed metal precursor solution may then be added to the support, optionally a modified support, followed by drying and calcining to form the final catalyst composition as described above.

The specific precursors used in the various embodiments of the invention may vary widely. Suitable metal precursors may include, for example, metal halides, amine solubilized metal hydroxides, metal nitrates, metal acetates, or metal oxalates. For example, suitable compounds for platinum precursors and palladium precursors include chloroplatinic acid, ammonium chloroplatinate, amine solubilized platinum hydroxide, platinum nitrate, platinum tetra ammonium nitrate, platinum chloride, platinum oxalate, palladium nitrate, palladium tetra ammonium nitrate, palladium chloride, palladium oxalate, sodium palladium chloride, sodium platinum chloride, and platinum ammonium nitrate, $Pt(NH_3)_4(NO_4)_2$. Generally, both from the point of view of economics and environmental aspects, aqueous solutions of soluble compounds of platinum and palladium are preferred. In one embodiment, the precious metal precursor is not a metal halide and is substantially free of metal halides, while in other embodiments, as described above, the precious metal precursor is a halide.

In another example, the second and third metals are co-impregnated with the precursor to $WO_3$ on the support, optionally forming a mixed oxide with $WO_3$, e.g., cobalt tungstate, followed by drying and calcination. The resulting modified support may be impregnated, preferably in a single impregnation step or multiple impregnation steps, with one or more of the first, second and third metals, followed by a second drying and calcination step. In this manner, cobalt tungstate may be formed on the modified support. Again, the temperature of the second calcining step preferably is less than the temperature of the first calcining step.

Catalyst

Due to the use of the halide precursors in the processes of the present invention, the resulting catalyst may have a halide concentration, in particular chloride concentration, that is greater than 10 wppm, e.g., greater than 100 wppm, or 200 wppm. In terms of ranges the halide concentration may be from 10 to 500 wppm, e.g., from 100 to 500 wppm or from 100 to 200 wppm. The halide concentration may be in an amount that does not impact the catalyst performance in terms of conversion, selectivity and/or productivity.

The catalysts prepared by the processes of the invention preferably include at least one precious metal impregnated on the catalyst support. The precious metal may be selected, for example, from rhodium, rhenium, ruthenium, platinum, palladium, osmium, iridium and gold. Preferred precious metals for the catalysts of the invention include palladium, platinum, and rhodium. The precious metal preferably is catalytically active in the hydrogenation of a carboxylic acid and/or its ester to the corresponding alcohol(s). The precious metal may be in elemental form or in molecular form, e.g., an oxide of the precious metal. The catalyst comprises such precious metals in an amount less than 5 wt. %, e.g., less than 3 wt. %, less than 2 wt. %, less than 1 wt. % or less than 0.5 wt. %. In terms of ranges, the catalyst may comprise the precious metal in an amount from 0.05 to 10 wt. %, e.g. from 0.1 to 5 wt. %, or from 0.1 to 3 wt. %, based on the total weight of the catalyst. In some embodiments, the metal loading of the precious metal may be less than the metal loadings of the one or more active metals.

In addition to the precious metal, the catalyst includes one or more active metals disposed on the modified support. In one embodiment, the modified support also comprises one or more active metals, such as cobalt and tin. Without being bound by theory, the active metals when part of the modified support may disperse the support modifier metal or oxide thereof on the support. An active metal is part of the modified support when it is impregnated and calcined on the support prior to the impregnation or introduction of the precious metal to the modified support. The same active metals may be part of the modified support and disposed on the support modifier. In particular, it may be preferred to use cobalt and tin.

As used herein, active metals refer to catalytically active metals that improve the conversion, selectivity and/or productivity of the catalyst and may include precious or non-precious active metals. Thus, a catalyst comprising a precious metal and an active metal may include: (i) one (or more) precious metals and one (or more) non-precious active metals, or (ii) may comprise two (or more) precious metals. Thus, precious metals are included herein as exemplary active metals. Further, it should be understood that use of the term "active metal" to refer to some metals in the catalysts of the invention is not meant to suggest that the precious metal that is also included in the inventive catalysts is not catalytically active.

In one embodiment, the one or more active metals included in the catalyst are selected from the group consisting of copper, iron, cobalt, vanadium, nickel, titanium, zinc, chromium, molybdenum, tungsten, tin, lanthanum, cerium, manganese, any of the aforementioned precious metals, in particular rhenium, ruthenium, and gold, and combinations thereof. Preferably, however, the one or more active metals do not include any precious metals, and thus include copper, iron, cobalt, vanadium, nickel, titanium, zinc, chromium, molybdenum, tungsten, tin, lanthanum, cerium, manganese, and combinations thereof. More preferably, the one or more active metals are selected from the group consisting of copper, iron, cobalt, nickel, chromium, molybdenum, tungsten and tin, and more preferably the one or more active metals are selected from cobalt, tin and tungsten. In one embodiment, the active metal may comprise tin in combination with at least one other active metal. The one or more active metals may be in elemental form or in molecular form, e.g., an oxide of the active metal, or a combination thereof.

The total weight of all the active metals, including the aforementioned precious metal, present in the catalyst preferably is from 0.1 to 25 wt. %, e.g., from 0.5 to 15 wt. %, or from 1.0 to 10 wt. %. In one embodiment, the catalyst may comprise from cobalt in an amount from 0.5 to 20 wt. %, e.g., preferably from 4.1 to 20 wt. %, and tin in an amount from 0.5 to 20 wt. %, e.g., preferably from 0.5 to 3.5 wt. %. The active metals for purposes of the present invention may be disposed on the modified support and may be part of the modified support. The total weight of the active metal may include the combined weight of the metal in the modified support and the metal disposed on the modified support. Thus, for example, the modified support may comprise from 0.1 to 15 wt. %, e.g. from 0.5 to 10 wt. %, of the one or more active metals and the one or more active metals disposed on the modified support may be present in an amount from 0.1 to 15 wt. %, e.g., from 0.5 to 10 wt. %, provided that the total metal loading of the one or more active metals is less than 25 wt. %. For purposes of the present specification, unless otherwise indicated, weight percent is based on the total weight the catalyst including metal and support.

In some embodiments, the catalyst contains at least two active metals in addition to the precious metal. The at least two active metals may be selected from any of the active metals identified above, so long as they are not the same as the precious metal or each other. Additional active metals may also be used in some embodiments. Thus, in some embodiments, there may be multiple active metals on the support in addition to the precious metal.

Preferred bimetallic (precious metal+active metal) combinations for some exemplary catalyst compositions include platinum/tin, platinum/ruthenium, platinum/rhenium, platinum/cobalt, platinum/nickel, palladium/ruthenium, palladium/rhenium, palladium/cobalt, palladium/copper, palladium/nickel, ruthenium/cobalt, gold/palladium, ruthenium/rhenium, ruthenium/iron, rhodium/iron, rhodium/cobalt, rhodium/nickel and rhodium/tin. In some embodiments, the catalyst comprises three metals on a support, e.g., one precious metal and two active metals. Exemplary tertiary combinations may include palladium/rhenium/tin, palladium/rhenium/cobalt, palladium/rhenium/nickel, palladium/cobalt/tin, platinum/tin/palladium, platinum/tin/rhodium, platinum/tin/gold, platinum/tin/iridium, platinum/cobalt/tin, platinum/tin/copper, platinum/tin/chromium, platinum/tin/zinc, platinum/tin/nickel, rhodium/nickel/tin, rhodium/cobalt/tin and rhodium/iron/tin. In one preferred embodiment, the tertiary combination comprises cobalt or tin or both cobalt and tin. In some embodiments, the catalyst may comprise more than three metals on the support.

When the catalyst comprises a precious metal and one active metal on a support, the active metal is present in an amount from 0.1 to 20 wt. %, e.g., from 0.1 to 10 wt. %, or from 0.1 to 7.5 wt. %. When the catalyst comprises two or more active metals in addition to the precious metal, e.g., a first active metal and a second active metal, the first active metal may be present in the catalyst in an amount from 0.05 to 20 wt. %, e.g. from 0.1 to 10 wt. %, or from 0.5 to 5 wt. %. The second active metal may be present in an amount from 0.05 to 20 wt. %, e.g., from 0.1 to 10 wt. %, or from 0.5 to 7.5 wt. %. If the catalyst further comprises a third active metal, the third active metal may be present in an amount from 0.05 to 20 wt. %, e.g., from 0.05 to 10 wt. %, or from 0.05 to 7.5 wt. %. When the second or third active metal is cobalt, in one embodiment, the metal loading may be from 4.1 to 20 wt. %, e.g., from 4.1 to 10 wt. % or from 4.1 to 7.5 wt. %. The active metals may be alloyed with one another or may comprise a non-alloyed metal solution, a metal mixture or be present as one or more metal oxides.

The preferred metal ratios may vary somewhat depending on the active metals used in the catalyst. In some embodiments, the mole ratio of the precious metal to the one or more active metals is from 10:1 to 1:10, e.g., from 4:1 to 1:4, from 2:1 to 1:2 or from 1.5:1 to 1:1.5. In another embodiment, the precious metal may be present in an amount from 0.1 to 5 wt. %, the first active metal in an amount from 0.5 to 20 wt. % and the second active metal in an amount from 0.5 to 20 wt. %, based on the total weight of the catalyst. In another embodiment, the precious metal is present in an amount from 0.1 to 5 wt. %, the first active metal in an amount from 0.5 to 15 wt. % and the second active metal in an amount from 0.5 to 15 wt. %.

In one embodiment, the first and second active metals are present as cobalt and tin, and, when added to the catalyst together and calcined together, are present at a cobalt to tin molar ratio from 6:1 to 1:6 or from 3:1 to 1:3. The cobalt and tin may be present in substantially equimolar amounts, when added to the catalyst together and calcination together. In another embodiment, when cobalt is added to the support material initially and calcined as part of the modified support and tin is subsequently added to the modified support, it is preferred to have a cobalt to tin molar that is greater than 4:1, e.g., greater than 6:1 or greater than 11:1. Without being bound by theory the excess cobalt, based on molar amount relative to tin, may improve the multifunctionality of the catalyst.

Support Materials

The catalysts of the present invention comprise a suitable support material, preferably a modified support material. In one embodiment, the support material may be an inorganic oxide. In one embodiment, the support material may be selected from the group consisting of silica, alumina, titania, silica/alumina, pyrogenic silica, high purity silica, zirconia, carbon (e.g., carbon black or activated carbon), zeolites and mixtures thereof. Preferably, the support material comprises a siliceous support material such as silica, pyrogenic silica, or high purity silica. In one embodiment the siliceous support material is substantially free of alkaline earth metals, such as magnesium and calcium. In preferred embodiments, the support material is present in an amount from 25 wt. % to 99 wt. %, e.g., from 30 wt. % to 98 wt. % or from 35 wt. % to 95 wt. %, based on the total weight of the catalyst.

In preferred embodiments, the support material comprises a siliceous support material, e.g., silica, having a surface area of at least 50 $m^2/g$, e.g., at least 100 $m^2/g$, or at least 150 $m^2/g$. In terms of ranges, the siliceous support material preferably has a surface area from 50 to 600 $m^2/g$, e.g., from 100 to 500 $m^2/g$ or from 100 to 300 $m^2/g$. High surface area silica, as used throughout the application, refers to silica having a surface area of at least 150 $m^2/g$. For purposes of the present specification, surface area refers to BET nitrogen surface area, meaning the surface area as determined by ASTM D6556-04, the entirety of which is incorporated herein by reference.

The preferred siliceous support material also preferably has an average pore diameter from 5 to 100 nm, e.g., from 5 to 30 nm, from 5 to 25 nm or from 5 to 10 nm, as determined by mercury intrusion porosimetry, and an average pore volume from 0.5 to 2.0 $cm^3/g$, e.g., from 0.7 to 1.5 $cm^3/g$ or from 0.8 to 1.3 $cm^3/g$, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the siliceous support material has a morphology that allows for a packing density from 0.1 to 1.0 $g/cm^3$, e.g., from 0.2 to 0.9 $g/cm^3$ or from 0.3 to 0.8 $g/cm^3$. In terms of size, the silica support material preferably has an average particle size, meaning the average diameter for spherical particles or average longest dimension for non-spherical particles, from 0.01 to 1.0 cm, e.g., from 0.1 to 0.7 cm or from 0.2 to 0.5 cm. Since the precious metal and the one or more active metals that are disposed on the support are generally in the form of very small metal (or metal oxide) particles or crystallites relative to the size of the support, these metals should not substantially impact the size of the overall catalyst particles. Thus, the above particle sizes generally apply to both the size of the support as well as to the final catalyst particles, although the catalyst particles are preferably processed to form much larger catalyst particles, e.g., extruded to form catalyst pellets.

Support Modifiers

The support material preferably comprises a support modifier. A support modifier may adjust the acidity of the support material. In one embodiment, a support modifier comprises a metal selected from the group consisting of tungsten, molybdenum, vanadium, niobium, and tantalum. The metal for the support modifier may be an oxide thereof. In one embodiment, the support modifiers are present in an amount from 0.1 wt. % to 50 wt. %, e.g., from 0.2 wt. % to 25 wt. %, from 0.5 wt. % to 20 wt. %, or from 1 wt. % to 15 wt. %, based on the total weight of the catalyst. When the support modifier comprises tungsten, molybdenum, and vanadium, the support modifier may be present in an amount from 0.1 to 40 wt. %, e.g., from 0.1 to 30 wt. % or from 10 to 25 wt. %, based on the total weight of the catalyst.

As indicated, the support modifiers may adjust the acidity of the support. For example, the acid sites, e.g., Brønsted acid sites or Lewis acid sites, on the support material may be adjusted by the support modifier to favor selectivity to ethanol during the hydrogenation of acetic acid and/or esters thereof. The acidity of the support material may be adjusted by optimizing surface acidity of the support material. The support material may also be adjusted by having the support modifier change the pKa of the support material. Unless the context indicates otherwise, the acidity of a surface or the number of acid sites thereupon may be determined by the technique described in F. Delannay, Ed., "Characterization of Heterogeneous Catalysts"; Chapter III: Measurement of Acidity of Surfaces, p. 370-404; Marcel Dekker, Inc., N.Y. 1984, the entirety of which is incorporated herein by reference. In general, the surface acidity of the support may be adjusted based on the composition of the feed stream being sent to the hydrogenation process in order to maximize alcohol production, e.g., ethanol production.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIII metals, aluminum oxides, and mixtures thereof. In one embodiment, the support modifier comprises metal selected from the group consisting of tungsten, molybdenum, vanadium, niobium, and tantalum.

In one embodiment, the acidic modifier may also include those selected from the group consisting of $WO_3$, $MoO_3$, $V_2O_5$, $VO_2$, $V_2O_3$, $Nb_2O_5$, $Ta_2O_5$, FeO, $Fe_3O_4$, $Fe_2O_3$, $Cr_2O_3$, $MnO_2$, CoO, $Co_2O_3$, and $Bi_2O_3$. Reduced tungsten oxides or molybdenum oxides may also be employed, such as, for example, one or more of $W_{20}O_{58}$, $WO_2$, $W_{49}O_{119}$, $W_{50}O_{148}$, $W_{18}O_{49}$, $Mo_9O_{26}$, $Mo_8O_{23}$, $Mo_5O_{14}$, $Mo_{17}O_{47}$, $Mo_4O_{11}$, or $MoO_2$. In one embodiment, the tungsten oxide may be cubic tungsten oxide ($H_{0.5}WO_3$). It has now surprisingly and unexpectedly been discovered that the use of such metal oxide support modifiers in combination with a precious metal and one or more active metals may result in catalysts having multifunctionality, and which may be suitable for converting a carboxylic acid, such as acetic acid, as well as corresponding esters thereof, e.g., ethyl acetate, to one or more hydrogenation products, such as ethanol, under hydrogenation conditions.

In other embodiments, the acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Acidic support modifiers include those selected from the group consisting of $TiO_2$, $ZrO_2$, $Nb_2O_5$, $Ta_2O_5$, and $Al_2O_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. The basic support modifier may be selected from the group consisting of oxides and metasilicates of any of sodium, potassium, magnesium, calcium, scandium, yttrium, and zinc, as well as mixtures of any of the foregoing. In one embodiment, the basic support modifier is a calcium silicate, such as calcium metasilicate ($CaSiO_3$). The calcium metasilicate may be crystalline or amorphous.

In some embodiments, the acidic support modifier comprises a mixed metal oxide comprising at least one of the active metals and an oxide anion of a Group IVB, VB, VIB, VIII metal, such as tungsten, molybdenum, vanadium, niobium or tantalum. The oxide anion, for example, may be in the form of a tungstate, molybdate, vanadate, or niobate. Exemplary mixed metal oxides include cobalt tungstate, copper tungstate, iron tungstate, zirconium tungstate, manganese tungstate, cobalt molybdate, copper molybdate, iron molybdate, zirconium molybdate, manganese molybdate, cobalt vanadate, copper vanadate, iron vanadate, zirconium vanadate, manganese vanadate, cobalt niobate, copper niobate, iron niobate, zirconium niobate, manganese niobate, cobalt tantalate, copper tantalate, iron tantalate, zirconium tantalate, and/or manganese tantalate. In one embodiment, the catalyst does not comprise tin tungstate and is substantially free of tin tungstate. It has now been discovered that catalysts containing such mixed metal support modifiers may provide the desired degree of multifunctionality at increased conversion, e.g., increased ester conversion, and with reduced byproduct formation, e.g., reduced diethyl ether formation.

In one embodiment, the catalyst comprises from 0.25 to 1.25 wt. % platinum, from 1 to 10 wt. % cobalt, and from 1 to 10 wt. % tin on a silica or a silica-alumina support material. The cobalt and tin may be disposed on the support material and may be part of the modified support. The support material may comprise from 5 to 15 wt. % acidic support modifiers, such as $WO_3$, $V_2O_5$ and/or $MoO_3$. In one embodiment, the acidic modifier may comprise cobalt tungstate, e.g., in an amount from 0.1 to 20 wt. %, or from 5 to 15 wt. %.

In some embodiments, the modified support comprises one or more active metals in addition to one or more acidic modifiers. The modified support may, for example, comprise one or more active metals selected from copper, iron, cobalt, vanadium, nickel, titanium, zinc, chromium, molybdenum, tungsten, tin, lanthanum, cerium, and manganese. For example, the support may comprise an active metal, preferably not a precious metal, and an acidic or basic support modifier. Preferably, the support modifier comprises a support modifier metal selected from the group consisting of tungsten, molybdenum, vanadium, niobium, and tantalum. In this aspect, the final catalyst composition comprises a precious metal, and one or more active metals disposed on the modified support. In a preferred embodiment, at least one of the active metals in the modified support is the same as at least one of the active metals disposed on the support. For example, the catalyst may comprise a support modified with cobalt, tin and tungsten (optionally as $WO_3$, $H_{0.5}WO_3$, $HWO_4$, and/or as cobalt tungstate). In this example, the catalyst further comprises a precious metal, e.g., palladium, platinum or rhodium, and at least one active metal, e.g., cobalt and/or tin, disposed on the modified support.

Without being by bound theory, it is believed that the presence of tin tungstate on the modified support or catalyst tends to decrease catalytic activity in the conversion of acetic acid to ethanol. When used on the modified support, tin does contribute to improved catalytic activity and catalyst lifetime. However, when tin is present with tungsten, the undesirable tin tungstate species may form. To prevent the formation of tin tungstate, it has been found the use of cobalt may inhibit the formation of tin tungstate. This allows the preferential formation of cobalt tungstate over tin tungstate. In addition, this allows the use of tin on the modified support to thus maintain sufficient catalyst activity and catalyst lifetime. In one embodiment, the modified support comprises cobalt tungstate and tin, but the modified support is substantially free of tin tungstate.

Use of Catalyst to Hydrogenate Acetic Acid

One advantage of catalysts of the present invention is the stability or activity of the catalyst for producing ethanol. Accordingly, it can be appreciated that the catalysts of the present invention are fully capable of being used in commercial scale industrial applications for hydrogenation of acetic acid, particularly in the production of ethanol. In particular, it is possible to achieve such a degree of stability such that catalyst activity will have a rate of productivity decline that is less than 6% per 100 hours of catalyst usage, e.g., less than 3% per 100 hours or less than 1.5% per 100 hours. Preferably, the rate of productivity decline is determined once the catalyst has achieved steady-state conditions.

After the washing, drying and calcining of the catalyst is completed, the catalyst may be reduced in order to activate it. Reduction is carried out in the presence of a reducing gas, preferably hydrogen. The reducing gas is optionally continuously passed over the catalyst at an initial ambient temperature that is increased up to 400° C. In one embodiment, the reduction is carried out after the catalyst has been loaded into the reaction vessel where the hydrogenation will be carried out.

In one embodiment the invention is to a process for producing ethanol by hydrogenating a feed stream comprising compounds selected from acetic acid, ethyl acetate and mixtures thereof in the presence of any of the above-described catalysts. One particular preferred reaction is to make ethanol from acetic acid. The hydrogenation reaction may be represented as follows:

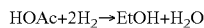

$$HOAc + 2H_2 \rightarrow EtOH + H_2O$$

In some embodiments, the catalyst may be characterized as a bifunctional catalyst in that it effectively catalyzes the hydrogenation of acetic acid to ethanol as well as the conversion of ethyl acetate to one or more products, preferably ethanol.

The raw materials, acetic acid and hydrogen, fed to the reactor used in connection with the process of this invention may be derived from any suitable source including natural gas, petroleum, coal, biomass, and so forth. As examples, acetic acid may be produced via methanol carbonylation, acetaldehyde oxidation, ethane oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from other carbon sources have drawn increasing interest. In particular, when petroleum is relatively expensive, it may become advantageous to produce acetic acid from synthesis gas ("syngas") that is derived from other available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Biomass-derived syngas has a detectable $^{14}C$ isotope content as compared to fossil fuels such as coal or natural gas. An equilibrium forms in the Earth's atmosphere between constant new formation and constant degradation, and so the proportion of the $^{14}C$ nuclei in the carbon in the atmosphere on Earth is constant over long periods. The same distribution ratio $n^{14}C:n^{12}C$ ratio is established in living organisms as is present in the surrounding atmosphere, which stops at death and $^{14}C$ decomposes at a half life of about 6000 years. Methanol, acetic acid and/or ethanol formed from biomass-derived syngas would be expected to have a $^{14}C$ content that is substantially similar to living organisms. For example, the $^{14}C:^{12}C$ ratio of the methanol, acetic acid and/or ethanol may be from one half to about 1 of the $^{14}C:^{12}C$ ratio for living organisms. In other embodiments, the syngas, methanol, acetic acid and/or ethanol described herein are derived wholly from fossil fuels, i.e. carbon sources produced over 60,000 years ago, may have no detectable $^{14}C$ content.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum,* and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola.* Optionally, in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. No. 6,509,180, and U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. Another biomass source is black liquor, which is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form syngas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into syngas, and U.S. Pat. No. 6,685,754, which discloses a method for the production of a hydrogen-containing gas composition, such as a syngas including hydrogen and carbon monoxide, are incorporated herein by reference in their entireties.

The acetic acid fed to the hydrogenation reactor may also comprise other carboxylic acids and anhydrides, as well as aldehyde and/or ketones, such as acetaldehyde and acetone. Preferably, the feed stream comprises acetic acid and ethyl acetate. A suitable acetic acid feed stream comprises one or more of the compounds selected from the group consisting of acetic acid, acetic anhydride, acetaldehyde, ethyl acetate, diethyl acetal, diethyl ether, and mixtures thereof. These other compounds may also be hydrogenated in the processes of the present invention. In some embodiments, the presence of carboxylic acids, such as propanoic acid or its aldehyde, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the hydrogenation reactor without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

The reactor, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles. In some embodiments, multiple catalyst beds are employed in the same reactor or in different reactors, e.g., in series. For example, in one embodiment, a first catalyst functions in a first catalyst stage as a catalyst for the hydrogenation of a carboxylic acid, e.g., acetic acid, to its corresponding alcohol, e.g., ethanol, and a second bifunctional catalyst is employed in the second stage for converting unreacted acetic acid to ethanol as well as converting byproduct ester, e.g., ethyl acetate, to additional products, preferably to ethanol. The catalysts of the invention may be employed in either or both the first and/or second stages of such reaction systems.

The hydrogenation in the reactor may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 2000 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 18:1 to 2:1. Most preferably, the molar ratio of hydrogen to acetic acid is greater than 2:1, e.g., greater than 4:1 or greater than 8:1. For a mixed feed stream, the molar ratio of hydrogen to ethyl acetate may be greater than 5:1, e.g., greater than 10:1 or greater than 15:1.

Contact or residence time can also vary widely, depending upon such variables as amount of feed stream (acetic acid and/or ethyl acetate), catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

In particular, by employing the catalysts of the invention, the hydrogenation of acetic acid and/or ethyl acetate may achieve favorable conversion and favorable selectivity and productivity to ethanol in the reactor. For purposes of the present invention, the term "conversion" refers to the amount of acetic acid or ethyl acetate, whichever is specified, in the feed that is converted to a compound other than acetic acid or ethyl acetate, respectively. Conversion is expressed as a percentage based on acetic acid or ethyl acetate in the feed. The acetic acid conversion may be at least 20%, more preferably at least 60%, at least 75%, at least 80%, at least 90%, at least 95% or at least 99%.

During the hydrogenation of acetic acid, ethyl acetate may be produced as a byproduct. Without consuming any ethyl acetate from the mixed vapor phase reactants, the conversion of ethyl acetate would be deemed negative. Some of the catalysts described herein are monofunctional in nature and are effective for converting acetic acid to ethanol, but not for converting ethyl acetate. The use of monofunctional catalysts may result in the undesirable build up of ethyl acetate in the system, particularly for systems employing one or more recycle streams that contain ethyl acetate to the reactor.

The preferred catalysts of the invention, however, are multifunctional in that they effectively catalyze the conversion of acetic acid to ethanol as well as the conversion of an alkyl acetate, such as ethyl acetate, to one or more products other than that alkyl acetate. The multifunctional catalyst is preferably effective for consuming ethyl acetate at a rate sufficiently great so as to at least offset the rate of ethyl acetate production, thereby resulting in a non-negative ethyl acetate conversion, i.e., no net increase in ethyl acetate is realized. The use of such catalysts may result, for example, in an ethyl acetate conversion that is effectively 0% or that is greater than 0%. In some embodiments, the catalysts of the invention are effective in providing ethyl acetate conversions of at least 0%, e.g., at least 5%, at least 10%, at least 15%, at least 20%, or at least 35%.

In continuous processes, the ethyl acetate being added (e.g., recycled) to the hydrogenation reactor and ethyl acetate leaving the reactor in the crude product preferably approaches a certain level after the process reaches equilibrium. The use of a multifunctional catalyst that catalyzes the conversion of ethyl acetate as well as acetic acid results in a lower amount of ethyl acetate added to the reactor and less ethyl acetate produced relative to monofunctional catalysts. In preferred embodiments, the concentration of ethyl acetate in the mixed feed and crude product is less than 40 wt. %, less than 25 wt. % or less than 15 wt. %, after equilibrium has been achieved. In preferred embodiments, the process forms a crude product comprising ethanol and ethyl acetate, and the crude product has an ethyl acetate steady state concentration from 0.1 to 40 wt. %, e.g., from 0.1 to 20 wt. % or from 0.1 to 15 wt. %, optionally where the ethyl acetate is separated and recycled to the reactor optionally resulting in no net increase or decrease in ethyl acetate production.

Although catalysts that have high acetic acid conversions are desirable, such as at least 60%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid and/or ethyl acetate. It should be understood that each compound converted from acetic acid and/or ethyl acetate has an independent selectivity and that selectivity is independent of conversion. For example, if 60 mole % of the converted acetic acid is converted to ethanol, we refer to the ethanol selectivity as 60%. For purposes of the present invention, the total selectivity is based on the combined converted acetic acid and ethyl acetate. Preferably, total selectivity to ethanol is at least 60%, e.g., at least 70%, or at least 80%, at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

In various embodiments of the present invention, the crude ethanol product produced by the reactor, before any subsequent processing, such as purification and separation, will typically comprise unreacted acetic acid, ethanol and water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 1 to 25 | 3 to 20 | 5 to 18 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product may comprise acetic acid in an amount less than 20 wt. %, e.g., of less than 15 wt. %, less than 10 wt. % or less than 5 wt. %. In terms of ranges, the acetic acid concentration of Table 1 may range from 0.1 wt. % to 20 wt. %, e.g., 0.1 wt. % to 15 wt. %, from 0.1 wt. % to 10 wt. % or from 0.1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is greater than 75%, e.g., greater than 85% or greater than 90%.

An ethanol product may be recovered from the crude ethanol product produced by the reactor using the catalyst of the present invention may be recovered using several different techniques.

The ethanol product may be an industrial grade ethanol comprising from 75 to 96 wt. % ethanol, e.g., from 80 to 96 wt. % or from 85 to 96 wt. % ethanol, based on the total weight of the ethanol product. The industrial grade ethanol may have a water concentration of less than 12 wt. % water, e.g., less than 8 wt. % or less than 3 wt. %. In some embodiments, when further water separation is used, the ethanol product preferably contains ethanol in an amount that is greater than 96 wt. %, e.g., greater than 98 wt. % or greater than 99.5 wt. %. The ethanol product having further water separation preferably comprises less than 3 wt. % water, e.g., less than 2 wt. % or less than 0.5 wt. %.

The finished ethanol composition produced by the embodiments of the present invention may be used in a variety of applications including fuels, solvents, chemical feedstocks, pharmaceutical products, cleansers, sanitizers, hydrogen transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the finished ethanol composition may be esterified with acetic acid. In another application, the finished ethanol composition may be dehydrated to produce ethylene. Any known dehydration catalyst, such as zeolite catalysts or phosphotungstic acid catalysts, can be employed to dehydrate ethanol, as described in U.S. Pub. Nos. 2010/0030002 and 2010/0030001 and WO2010146332, the entire contents and disclosures of which are hereby incorporated by reference.

Catalyst Regeneration

The catalysts of the invention are particularly robust and have long catalyst lifetimes. Nevertheless, over periods of extended usage, the activity of the catalysts of the invention may gradually be reduced. Accordingly, in another embodiment of the invention, the invention relates to a process for regenerating a spent hydrogenation catalyst, comprising contacting a carboxylic acid and hydrogen in a hydrogenation reactor with a hydrogenation catalyst under conditions effective to form a hydrogenation product and the spent hydrogenation catalyst; and treating the spent hydrogenation catalyst with a regenerating medium at a temperature greater than 200° C., optionally from 300° C. to 600° C., under conditions effective to form a regenerated hydrogenation catalyst having greater catalytic activity than the spent hydrogenation catalyst, wherein the hydrogenation catalyst comprises a precious metal and one or more active metals on a support. In this context, by "spent" it is meant a catalyst having reduced conversion and/or reduced selectivity for the desired product, e.g., ethanol, relative to an earlier usage period for the same catalyst, wherein the reduced selectivity and/or conversion cannot be recovered by increasing reactor temperature up to designed limits.

In another embodiment, the invention is to a process for regenerating a spent catalyst comprising (a) contacting a carboxylic acid and hydrogen in a hydrogenation reactor with a hydrogenation catalyst under conditions effective to form a hydrogenation product and the spent hydrogenation catalyst; and (b) treating the spent hydrogenation catalyst with a regenerating medium at a temperature greater than 200° C., optionally from 300° C. to 600° C., under conditions effective to form a regenerated hydrogenation catalyst having greater catalytic activity than the spent hydrogenation catalyst, wherein the hydrogenation catalyst comprises a precious metal and one or more active metals on a support. The treating may occur within the hydrogenation reactor, or external to the hydrogenation reactor. For example, the treating may occur in a regeneration unit, in which case the process further comprises the steps of directing the spent hydrogenation catalyst from the hydrogenation reactor to the regeneration unit, and directing the regenerated hydrogenation catalyst from the regeneration unit to the hydrogenation reactor.

The regenerating medium may vary depending on whether it is desired to merely "strip" the catalyst, for example of carbonaceous materials, or whether full regeneration is desired. Depending on the condition of the spent catalyst, the regenerating medium may be selected from steam, oxygen (optionally in the form of air, diluted air or an oxygen/nitrogen mixture optionally with variable $O_2/N_2$ ratio during regeneration treatment), or hydrogen. Preferably, the regeneration medium is substantially free of the carboxylic acid reactant, optionally comprising less than 10 wt. % carboxylic acids, less than 5 wt. % carboxylic acids, or less than 1 wt. % carboxylic acids, e.g., acetic acid. The treating step may occur, for example, at a pressure ranging from 0.5 to 10 bar, e.g., from 0.8 to 8 bar or from 0.9 to 4 bar. The regenerating may occur, for example, over a period ranging from 10 to 200 hours, e.g., from 20 to 150 hours or from 50 to 100 hours. Preferably, the conditions employed in the treating step are sufficient to increase the carboxylic acid conversion, e.g., acetic acid conversion, and/or ethanol selectivity of the resulting regenerated hydrogenation catalyst by at least 25%, e.g., at least 50%, or at least 75%, relative to the conversion and selectivity of the spent catalyst. In another aspect, the spent catalyst has a reduced or lost ethanol selectivity relative to fresh catalyst, and the regenerated catalyst recovers at least 25%, at least 50% or at least 75% of the lost ethanol selectivity. Similarly, the spent catalyst may have a reduced or lost acetic acid conversion relative to fresh catalyst, and the regenerated catalyst recovers at least 25%, at least 50% or at least 75% of the lost acetic acid conversion.

If steam is employed as the regeneration medium, it may be desired to dry the regenerated hydrogenation catalyst prior to using the regenerated hydrogenation catalyst in the primary hydrogenation process. The drying is optionally performed at a temperature from 10 to 350° C., e.g., 50 to 250° C., from 70 to 180° C. or from 80 to 130° C., and optionally at an absolute pressure from 0.5 to 5 bar, e.g., from 0.8 to 2 bar, or from 0.9 to 1.5 bar, and optionally over a period of time from 10 to 50 hours, e.g., 10 to 20 hours, as described in US Pub. No. 2011/0144398, the entirety of which is incorporated herein by reference.

The following examples describe the catalyst and process of this invention.

EXAMPLES

Example 1

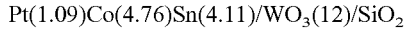

A metal impregnation solution was prepared. A tin salt solution was prepared by dissolving 1.86 g (5.31 mmol) of $Sn(IV)Cl_4 \cdot 5H_2O$ (solid) into 9 g of $DI\text{-}H_2O$. 3.6 g (12.36 mmol) of $Co(NO_3)_2 \cdot 6H_2O$ solid was added to the solution with stifling. A platinum salt solution was simultaneously prepared by dissolving 0.43 g (0.83 mmol Pt) of $H_2PtCl_6 \cdot xH_2O$ (solid, Pt: 38.2 wt. %) into 5 g of DI-$H_2O$. The platinum salt solution was added to the above Co/Sn solution. The mixture was stirred at 400 rpm for 5 minutes at room temperature.

The resulting solution was then added to 13.51 g of $WO_3$(12)/$SiO_2$ pellets formed according to Example 10 in a one-liter round flask by using incipient wetness techniques to provide a uniform distribution on the support. After adding the metal solution, the material was evacuated to dryness with a rotary evaporator at a bath temperature of 80° C. and vacuum at 72 mbar for 2 hours, followed by drying at 120° C. at 12 hours under circulating air and calcination at 350° C. for 8 hours. Temperature program: increase from room temperature to 160° C. at 3° C./min ramp, hold at 160° C. for 2 hours, increase from 160° C. to 350° C. at 3° C./min ramp, and hold at 350° C. for 8 hours.

Example 2

Pt(1.09)Co(3.75)Sn(3.25)/CoSnWO_3/SiO_2

A. Preparation of Modified Support: Co(3.75)Sn(3.25)WO_3(12)/SiO_2

A metal impregnation solution was prepared as follows. First, a solution of tin salt was prepared by dissolving 2.476 g of $Sn(II)Cl_2 \cdot 2H_2O$ (solid) into the 25 g of DI-$H_2O$. 7.5586 g of $Co(NO_3)_2 \cdot 6H_2O$ solid was add to the solution with stirring. After the Co salt was completely dissolved, 5.2574 g of ammonium metatungstate (AMT) was added to the solution. The mixture was then stirred at 400 rpm for another 5 minutes at room temperature.

The resulting solution was then added to 32.4 g $SiO_2$ support in a one-liter round flask by using incipient wetness technique to provide a uniform distribution on the support. After adding the metal solution, the material was evacuated to dryness using a rotary evaporator with bath temperature at 80° C. and vacuum at 72 mbar for 2 hours, followed by drying at 120° C. for 12 hours under circulating air and calcination at 600° C. for 6-8 hours. Temperature Program: increase from room temperature to 160° C. at 3° C./min ramp, hold at 160° C. for 2 hours; increase from 160° C. to 600° C. at 3° C./min ramp, hold at 600° C. for 6-8 hours.

B. Impregnation of Modified Support: Pt(1.09)Co(3.75)Sn(3.25)/CoSnWO_3/SiO_2

A tin salt solution was prepared by dissolving 0.619 g of $Sn(II)Cl_2 \cdot 2H_2O$ (solid) into 6 g of DI-$H_2O$. 1.8896 g of $Co(NO_3)_2 \cdot 6H_2O$ solid was add to the solution with stirring. A platinum salt solution was simultaneously prepared by dissolving 0.2855 g of $H_2PtCl_6 \cdot xH_2O$ (solid, Pt: 38.2 wt. %) into 3 g of DI-$H_2O$. The platinum salt solution was added to the above Co/Sn solution. The mixture was then stirred at 400 rpm for another 5 minutes at room temperature.

The resulting solution was then added to 9.191 g of CoSnWO_3/SiO_2 pellets formed as described above in a one-liter round flask by using incipient wetness technique to provide a uniform distribution on the support. After adding the metal solution, the material was evacuated to dryness with a rotary evaporator at a bath temperature of 80° C. and vacuum at 72 mbar for 2 hours, followed by drying at 120° C. for 12 hours under circulating air and calcination at 350° C. for 8 hours. Temperature Program: increase from room temperature to 160° C. at 3° C./min ramp, hold at 160° C. for 2 hours; increase from 160° C. to 350° C. at 3° C./min ramp, hold at 350° C. for 8 hours.

Example 3

Pt(1.09)Co(3.75)Sn(3.25)/CoSnWO_3/SiO_2

A. Preparation of Modified Support: Co(3.75)Sn(3.25)WO_3(12)/SiO_2

A metal impregnation solution was prepared as follows. First, a solution of tin salt was prepared by dissolving 3.9177 g of $Sn(IV)Cl_4 \cdot 5H_2O$ (solid) into the 25 g of DI-$H_2O$. 7.5586 g of $Co(NO_3)_2 \cdot 6H_2O$ solid was add to the solution with stifling. After the Co salt was completely dissolved, 5.2574 g of ammonium metatungstate (AMT) was added to the solution. The mixture was then stirred at 400 rpm for another 5 minutes at room temperature.

The resulting solution was then added to 32.4 g $SiO_2$ support in a one-liter round flask by using incipient wetness technique to provide a uniform distribution on the support. After adding the metal solution, the material was evacuated to dryness using a rotary evaporator with bath temperature at 80° C. and vacuum at 72 mbar for 2 hours, followed by drying at 120° C. for 12 hours under circulating air and calcination at 600° C. for 6-8 hours. Temperature Program: increase from room temperature to 160° C. at 3° C./min ramp, hold at 160° C. for 2 hours; increase from 160° C. to 600° C. at 3° C./min ramp, hold at 600° C. for 6-8 hours.

B. Impregnation of Modified Support: Pt(1.09)Co(3.75)Sn(3.25)/CoSnWO_3/SiO_2

A tin salt solution was prepared by dissolving 0.9794 g of $Sn(IV)Cl_4 \cdot 5H_2O$ (solid) into 6 g of DI-$H_2O$. 1.8896 g of $Co(NO_3)_2 \cdot 6H_2O$ solid was add to the solution with stirring. A platinum salt solution was simultaneously prepared by dissolving 0.2855 g of $H_2PtCl_6 \cdot XH_2O$ (solid, Pt: 38.2 wt. %) into 3 g of DI-$H_2O$. The platinum salt solution was added to the above Co/Sn solution. The mixture was then stirred at 400 rpm for another 5 minutes at room temperature.

The resulting solution was then added to 9.191 g of CoSnWO_3/SiO_2 pellets formed as described above in a one-liter round flask by using incipient wetness technique to provide a uniform distribution on the support. After adding the metal solution, the material was evacuated to dryness with a rotary evaporator at a bath temperature of 80° C. and vacuum at 72 mbar for 2 hours, followed by drying at 120° C. for 12 hours under circulating air and calcination at 350° C. for 8 hours. Temperature Program: increase from room temperature to 160° C. at 3° C./min ramp, hold at 160° C. for 2 hours; increase from 160° C. to 350° C. at 3° C./min ramp, hold at 350° C. for 8 hours.

Example 4

Pt(1.09)Co(3.75)Sn(3.25)/CoSnWO_3/SiO_2

A. Preparation of Modified Support: Co(3.75)Sn(3.25)WO_3(12)/SiO_2

A metal impregnation solution was prepared as follows. First, a solution of tin salt was prepared by adding 15.6708 g (0.0447 mol) of $Sn(IV)Cl_4 \cdot 5H_2O$ (solid) into 100 g of DI-$H_2O$. 30.23 g (0.1039 mol) of $Co(NO_3)_2 \cdot 6H_2O$ (solid) was added to the solution with stifling. After the cobalt salt was completely dissolved, 21.03 g (0.0854 mol of W) of AMT was added to the solution. The mixture was then stirred at 400 rpm for another 5 minutes at room temperature.

The resulting solution was then added to 129.6 g SiO2 support in a one-liter round flask by using incipient wetness techniques to provide a uniform distribution on the support. After adding the metal solution, the material was evacuated to dryness using a rotary evaporator with bath temperature at 80° C. and vacuum at 72 mbar for 2 hours, followed by drying at 120° C. for 12 hours under circulating air and calcination at 600° C. for 6-8 hours. Temperature Program: increase from room temperature to 160° C. at 3° C./min ramp, hold at 160° C. for 2 hours; increase from 160° C. to 600° C. at 3° C./min ramp, hold at 600° C. for 6-8 hours.

B. Impregnation of Modified Support: Pt(1.09)Co(3.75)Sn (3.25)/CoSnWO$_3$/SiO$_2$ A metal impregnation solution was prepared. A tin salt solution was prepared by dissolving 4.86 g (13.69 mmol) of Sn(IV)Cl$_4$.5H$_2$O (solid) into 29.4 g of DI-H$_2$O. 9.26 g (31.80 mmol) of Co(NO$_3$)$_2$.6H$_2$O (solid) was added to the solution with stirring. A platinum salt solution was simultaneously prepared by dissolving 1.4 g (2.70 mmol Pt) of H$_2$PtCl$_6$.XH$_2$O (solid, Pt: 38.2 wt. %) into 14.7 g of DI-H$_2$O. The platinum salt solution was added to the above Co/Sn solution. The mixture was stirred at 400 rpm for 5 minutes at room temperature. The resulting solution was then added to 45.04 g of CoSnWO$_3$/SiO$_2$ pellets formed as described above in a one-liter round flask by using incipient wetness techniques to provide a uniform distribution on the support. After adding the metal solution, the material was evacuated to dryness with a rotary evaporator at a bath temperature of 80° C. and vacuum at 72 mbar for 2 hours, followed by drying at 120° C. at 12 hours under circulating air and calcination at 350° C. for 8 hours. Temperature Program: increase from room temperature to 160° C. at 3° C./min ramp, hold at 160° C. for 2 hours; increase from 160° C. to 350° C. at 3° C./min ramp, hold at 350° C. for 8 hours.

Example 5

Performance Tests

The catalysts of Examples 1-4 were fed to a test unit using one of the following running conditions.

Reactor System and Catalytic Testing Conditions.

The test unit comprised four independent tubular fixed bed reactor systems with common temperature control, pressure and gas and liquid feeds. The reactors were made of ⅜ inch (0.95 cm) 316 SS tubing, and were 12⅛ inches (30.8 cm) in length. The vaporizers were made of ⅜ inch (0.95 cm) 316 SS tubing and were 12⅜ inches (31.45 cm) in length. The reactors, vaporizers, and their respective effluent transfer lines were electrically heated (heat tape).

The reactor effluents were routed to chilled water condensers and knock-out pots. Condensed liquids were collected automatically, and then manually drained from the knock-out pots as needed. Non-condensed gases were passed through a manual back pressure regulator (BPR) and then scrubbed through water and vented to the fume hood. For each Example, 15 ml of catalyst (3 mm pellets) was loaded into reactor. Both inlet and outlet of the reactor were filled with glass beads (3 mm) to form the fixed bed. The following running conditions for catalyst screening were used: T=275° C., P=300 psig (2068 kPag), [Feed]=0.138 ml/min (pump rate), and [H$_2$]=513 sccm, gas-hourly space velocity (GHSV)=2246 hr$^{-1}$. The mixed feed composition used for testing are summarized in the Table 2.

TABLE 2

Mixed Feed Composition for Catalyst Performance Evaluation

| H$_2$O (wt. %) | Acetaldehyde (wt. %) | Ethanol (wt. %) | Ethyl Acetate (wt. %) | Acetic Acid (wt. %) | Diethyl Acetal (wt. %) |
|---|---|---|---|---|---|
| 0.65 | 0.55 | 5.70 | 20.72 | 69.92 | 2.45 |

Running Condition 1: Catalyst was fed to a test unit in the manner described above for Examples 1-4, using the feed composition of TABLE 2.

Running Condition 2: Similar to Running Condition 1, except for catalyst usage. 10 mL of catalyst instead of 15 mL of catalyst was used resulting in an increase in superficial velocity to 3367 hr$^{-1}$.

The crude product was analyzed by gas chromatograph (Agilent GC Model 6850), equipped with a flame ionization detector. The GC analytical results of the liquid product effluent, excluding water, are provided below in TABLE 3. Diethyl ether and acetone were detected in concentrations were less than 0.1 wt. % respectively.

TABLE 3

Liquid Product Effluent Compositions
Examples 1-4

| Running Condition | Ex | EtOH (wt. %) | EtOAc (wt. %) | AcH (wt. %) | HOAc (wt. %) | Acetal (wt. %) |
|---|---|---|---|---|---|---|
| 1 | 1 | 62.7 | 13.7 | 0.9 | 0.4 | 0.1 |
| 1 | 2 | 63.1 | 14.1 | 0.8 | 0.2 | 0.1 |
| 1 | 3 | 65.3 | 12.5 | 0.9 | 0.2 | 0.1 |
| 2 | 4 | 58.2 | 17.7 | 0.8 | 0.5 | 0.3 |

Catalyst performance results were then calculated and are provided below in TABLE 4.

TABLE 4

Catalyst Performance Data Obtained Under Mixed Feed Conditions
Examples 1-4

| Running Condition | Ex | HOAc Conv. (%) | EtOAc Conv. (%) | EtOH Select. (mol %) | EtOH Prod. (g/kg/h) | EtOH Prod. (g/L/h) |
|---|---|---|---|---|---|---|
| 1 | 1 | 99.4 | 35.4 | 92.7 | 626.9 | 311.8 |
| 1 | 2 | 99.7 | 32.9 | 94.9 | 605.2 | 313.7 |
| 1 | 3 | 99.8 | 40.4 | 95.9 | 543.8 | 294.0 |
| 2 | 4 | 99.2 | 14.6 | 93.4 | 879.8 | 407.4 |

While the invention has been described in detail, modifications within the spirit and scope of the invention will be readily apparent to those skilled in the art. All publications and references discussed above are incorporated herein by reference. In addition, it should be understood that aspects of the invention and portions of various embodiments and various features recited may be combined or interchanged either in whole or in part. In the foregoing descriptions of the various embodiments, those embodiments which refer to another embodiment may be appropriately combined with other embodiments as will be appreciated by one skilled in the art. Furthermore, those skilled in the art will appreciate that the foregoing description is by way of example only, and is not intended to limit the invention.

We claim:

1. A process for forming a catalyst, the process comprising the steps of:
   (a) preparing a first solution comprising a first metal halide and a second metal precursor comprising a second metal oxalate, acetate, halide, or nitrate;
   (b) preparing a second solution comprising a precious metal halide, oxalate, acetate or nitrate;
   (c) impregnating a support comprising silica, cobalt tungstate and tin with the first solution and the second solution to form an impregnated support; and
   (d) drying and calcining the impregnated support to form the catalyst.

2. The process of claim 1, wherein the catalyst has a halide concentration that is greater than 10 wppm.

3. The process of claim 1, wherein the first solution is substantially free of acids selected from the group consisting of acetic acid, hydrochloric acid or nitric acid.

4. The process of claim 1, wherein the first solution and the second solution are simultaneously impregnated on the support.

5. The process of claim 1, wherein the precious metal is selected from the group consisting of rhodium, rhenium, ruthenium, platinum, palladium, osmium, iridium and gold.

6. The process of claim 1, wherein the first metal is selected from the group consisting of copper, iron, cobalt, vanadium, nickel, titanium, zinc, chromium, molybdenum, tungsten, tin, lanthanum, cerium, and manganese.

7. The process of claim 1, wherein the second metal is selected from the group consisting of copper, iron, cobalt, vanadium, nickel, titanium, zinc, chromium, molybdenum, tungsten, tin, lanthanum, cerium, and manganese.

8. The process of claim 1, wherein the precious metal is selected from the group consisting of rhodium, rhenium, ruthenium, platinum, palladium, osmium, iridium and gold, and the first metal and the second metal are selected from the group consisting of copper, iron, cobalt, vanadium, nickel, titanium, zinc, chromium, molybdenum, tungsten, tin, lanthanum, cerium, and manganese.

9. The process of claim 1, wherein the precious metal is selected from the group consisting of rhodium, rhenium, ruthenium, platinum, palladium, osmium, iridium and gold, and the first metal and the second metal are selected from the group consisting of copper, iron, cobalt, vanadium, nickel, titanium, zinc, chromium, molybdenum, tungsten, tin, lanthanum, cerium, and manganese, and wherein the precious metal is present in an amount from 0.1 to 5 wt. %, the first metal is present in an amount from 0.5 to 20 wt. % and the second metal is present in an amount from 0.5 to 20 wt. %, based on the total weight of the catalyst.

10. The process of claim 1, wherein the precious metal is present in an amount from 0.1 to 5 wt. %, the first metal is present in an amount from 0.5 to 20 wt. % and the second metal is present in an amount from 0.5 to 20 wt. %, based on the total weight of the catalyst.

11. The process of claim 1, wherein the precious metal is selected from the group consisting of rhodium, rhenium, ruthenium, platinum, palladium, osmium, iridium and gold, the first metal is cobalt and the second metal is tin.

12. The process of claim 1, wherein the precious metal is palladium, the first metal is tin and the second metal is cobalt.

13. The process of claim 1, wherein the precious metal is platinum, the first metal is tin and the second metal is cobalt.

14. A process for forming a catalyst, the process comprising the steps of:
   (a) preparing a first solution comprising a first metal halide and a second metal precursor comprising a second metal oxalate, acetate, halide, or nitrate;
   (b) preparing a second solution comprising a precious metal halide, oxalate, acetate or nitrate;
   (c) combining the second solution with the first solution to form a mixed metal precursor solution;
   (d) impregnating a support comprising silica, cobalt tungstate and tin with the mixed metal precursor solution to form an impregnated support; and
   (e) drying and calcining the impregnated support to form the catalyst.

* * * * *